(12) United States Patent
Okoro

(10) Patent No.: US 8,323,702 B2
(45) Date of Patent: Dec. 4, 2012

(54) COMPOSITION AND METHOD FOR TREATING ULCERS

(76) Inventor: Chuks I. Okoro, Lagos (NG)

( * ) Notice: Subject to any disclaimer, the term of this patent is extended or adjusted under 35 U.S.C. 154(b) by 343 days.

(21) Appl. No.: 12/656,412

(22) Filed: Jan. 28, 2010

(65) Prior Publication Data

US 2011/0183002 A1 Jul. 28, 2011

(51) Int. Cl.
*A61K 33/44* (2006.01)
*A61K 35/32* (2006.01)
*A61K 36/31* (2006.01)

(52) U.S. Cl. .................................................. 424/600

(58) Field of Classification Search .................. None
See application file for complete search history.

(56) References Cited

U.S. PATENT DOCUMENTS

| | | | |
|---|---|---|---|
| 4,957,741 | A | 9/1990 | Kamarei et al. |
| 5,066,496 | A | 11/1991 | Szabo et al. |
| 6,133,318 | A | 10/2000 | Hart |
| 6,399,325 | B1 | 6/2002 | Hinuma et al. |
| 7,262,194 | B2 | 8/2007 | Kyle et al. |
| 2003/0118563 | A1 | 6/2003 | Loeb |
| 2007/0027040 | A1 | 2/2007 | Krull et al. |
| 2007/0149417 | A1 | 6/2007 | Krull et al. |
| 2008/0038368 | A1 | 2/2008 | Geibel et al. |
| 2009/0194893 | A1 | 8/2009 | Asano et al. |
| 2009/0274660 | A1 | 11/2009 | Girsh |

FOREIGN PATENT DOCUMENTS

WO WO2007/015102 * 2/2007

OTHER PUBLICATIONS

English abstract : Karlina et al., RU2155591 (Sep. 2000).*
Warner, J. Olive oil may prevent ulcers. WebMD Health News, Feb. 13, 2007, www.webmd.com/digestive-disorders/news/20070213/olive-oil-may-prevent-ulcers.*
Shipley, W. C. California and Western Medicine, Editorial Comment, Feb. 1935, v. 42, iss. 2, p. 124-125.*
Gawron-Gzella, A.; et al. Przeglad Lekarski, 2005, vol. 62, iss. 10, p. 1185-1187 and certified English translation.*
Better Nutrition for Today's Living, v. 55, issue 5, p. 16, May 1993.*
Columbia Electronic Encyclopedia entry for Astringent (http://web.archive.org/web20010509211610/http://www.infoplease.com/ce6/sci/A0805129.html), accessed Jul. 9, 2012.*
The Doctors Book of Home Remedies Revised Edition, Rodale Press, 1990, p. 604.*

* cited by examiner

*Primary Examiner* — Mina Haghighatian
*Assistant Examiner* — Erin Hirt
(74) *Attorney, Agent, or Firm* — Richard C. Litman

(57) ABSTRACT

The composition for the treatment of ulcers includes ground charcoal, ground mustard seed and an edible salt dissolved or suspended in an edible oil. A single effective therapeutic dosage of the composition includes approximately 4,000 mg of the ground charcoal, approximately 2,500 mg of the ground mustard seed, approximately 550 mg of the edible salt, and approximately 15 ml of the edible oil. The effective therapeutic dosage is delivered to the patient orally, and may be provided to the patient as a tablet or capsule, or as a liquid mixture.

10 Claims, No Drawings

COMPOSITION AND METHOD FOR TREATING ULCERS

BACKGROUND OF THE INVENTION

1. Field of the Invention

The present invention relates to the treatment of ulcers, and particularly to a composition for treating ulcers containing ground charcoal, ground mustard seed and an edible salt dissolved or suspended in an edible oil.

2. Description of the Related Art

A peptic ulcer, also known as *ulcus pepticum* or peptic ulcer disease (PUD), is an ulcer (an ulcer is typically defined as mucosal erosions equal to or greater than 0.5 cm) of an area of the gastrointestinal tract that is usually acidic and, thus, extremely painful. As many as 80% of ulcers are associated with *Helicobacter pylori*, a spiral-shaped bacterium that lives in the acidic environment of the stomach. Ulcers can also be caused or worsened by drugs, such as aspirin.

Symptoms of a peptic ulcer include abdominal pain, bloating and abdominal fullness, waterbrash (a rush of saliva after an episode of regurgitation to dilute the acid in esophagus), nausea and copious vomiting, loss of appetite and weight loss, hematemesis (i.e., vomiting of blood), melena (tarry, foul-smelling feces due to oxidized iron from hemoglobin), and, rarely, gastric or duodenal perforation. The latter is extremely painful and requires immediate surgery.

Younger patients with ulcer-like symptoms are often treated with antacids or H2 antagonists before an esophago-gastroduodenoscopy (EGD) is undertaken. Bismuth compounds may actually reduce or even clear organisms, though it should be noted that the warning labels of some bismuth subsalicylate products indicate that the product should not be used by someone with an ulcer.

Patients who are taking nonsteroidal antiinflammatories (NSAIDs) may also be prescribed a prostaglandin analogue in order to help prevent peptic ulcers, which may be a side effect of the NSAIDs. When *H. pylori* infection is present, the most effective treatments are combinations of two antibiotics (e.g., clarithromycin, amoxicillin, tetracycline, metronidazole) and one proton pump inhibitor (PPI), sometimes together with a bismuth compound. In complicated, treatment-resistant cases, three antibiotics (e.g. amoxicillin+clarithromycin+metronidazole) may be used together with a PPI and sometimes with bismuth compound. An effective first-line therapy for uncomplicated cases would be amoxicillin+metronidazole+pantoprazole (a PPI). In the absence of *H. pylori*, long-term higher dose PPIs are often used.

Treatment of *H. pylori* usually leads to clearing of infection, relief of symptoms and eventual healing of ulcers. Recurrence of infection can occur and re-treatment may be required, if necessary with other antibiotics. Since the widespread use of PPIs in the 1990s, surgical procedures (such as "highly selective vagotomy") for uncomplicated peptic ulcers became obsolete.

Such treatments, however, are typically not easy for the patient and side effect free. Heavy dosages of antibiotics can cause further digestive problems for the patient, as well as cause the patient immunity-related problems as well as a host of various side effects associated with each drug. Further, the usage of varying types of antibiotics promotes the proliferation of antibiotic-resistant bacteria in the environment.

Thus, a composition and method for treating ulcers solving the aforementioned problems is desired.

SUMMARY OF THE INVENTION

The composition for treating ulcers includes ground charcoal, ground mustard seed and an edible salt dissolved or suspended in an edible oil. A single effective therapeutic dosage of the composition includes approximately 4,000 mg of the ground charcoal, approximately 2,500 mg of the ground mustard seed, approximately 550 mg of the edible salt, and approximately 15 ml of the edible oil. The effective therapeutic dosage is delivered to the patient orally, and may be provided to the patient as a tablet or capsule, or as a liquid mixture.

These and other features of the present invention will become readily apparent upon further review of the following specification.

DETAILED DESCRIPTION OF THE PREFERRED EMBODIMENT

The composition for treating ulcers includes ground charcoal, ground mustard seed and an edible salt dissolved or suspended in an edible oil. A single effective therapeutic dosage of the composition includes approximately 4,000 mg of the ground charcoal, approximately 2,500 mg of the ground mustard seed, approximately 550 mg of the edible salt, and approximately 15 ml of the edible oil.

Although any suitable type of ground charcoal may be utilized, the ground charcoal is preferably derived from cow bone. A cow bone is first washed, then dried and burned. The burned cow bone is then ground to form the ground charcoal. Any suitable type of ground mustard seed may be utilized. Similarly, any suitable type of edible salt, such as sodium chloride or the like, may be utilized. Further, it should be understood that any suitable type of edible oil, such as olive oil, canola oil, safflower oil or the like may be used.

The effective therapeutic dosage is delivered to the patient orally, and may be provided to the patient as a tablet or capsule, or as a liquid mixture. Preferably, one dosage is delivered to the patient per day, and treatment lasts for at least three successive days. Preferably, a full glass of water should be swallowed by the patient along with the effective therapeutic dosage, whether the dosage is provided in liquid form or as a capsule. For a capsule dosage, the ground charcoal, ground mustard seed, edible salt and edible oil may be contained within a gel capsule or the like, or bound into a solid tablet, as is well-known in the art.

It is to be understood that the present invention is not limited to the embodiment described above, but encompasses any and all embodiments within the scope of the following claims.

I claim:

1. A composition for treating ulcers, consisting essentially of:
   approximately 4,000 mg ground charcoal, wherein the ground charcoal is formed from burned and ground cow bone;
   approximately 2,500 mg ground mustard seed;
   approximately 550 mg edible salt; and
   15 ml edible olive oil, the charcoal, mustard seed and salt being dissolved in the edible oil.

2. The composition for treating ulcers as recited in claim 1, wherein the edible salt is sodium chloride.

3. A method for treating ulcers comprising the step of administering to a patient a therapeutically effective dosage of approximately 4,000 mg ground charcoal, wherein the ground charcoal is formed from burned and ground cow bone, approximately 2,500 mg ground mustard seed, approximately 550 mg of an edible salt dissolved in 15 mL of an edible oil for the treatment of ulcers.

4. The method for treating ulcers as recited in claim 3, wherein the step of administering to the patient the therapeutically effective dosage includes oral delivery to the patient.

5. The method for treating ulcers as recited in claim 4, wherein the therapeutically effective dosage is delivered to the patient as a liquid.

6. The method for treating ulcers as recited in claim 5, wherein the therapeutically effective dosage is delivered to the patient as a capsule.

7. A method of making a composition for the treatment of ulcers, comprising the steps of: preparing approximately 4,000 mg of ground charcoal, wherein the ground charcoal is formed from burned and ground cow bone; preparing approximately 2,500 mg of ground mustard seed; preparing approximately 550 mg of an edible salt; and dissolving the ground charcoal, the ground mustard seed, and the edible salt in approximately 15 mL of an edible oil.

8. The method of making a composition for the treatment of ulcers as recited in claim 7, wherein the step of preparing the ground charcoal comprises the steps of: providing a cow bone; cleaning the cow bone; burning the cow bone; and grinding the burned cow bone.

9. The method of making a composition for the treatment of ulcers as recited in claim 7, wherein the ground charcoal, the ground mustard seed and the edible salt are dissolved in 15 mL of olive oil.

10. The method of making a composition for the treatment of ulcers as recited in claim 7, wherein the ground charcoal, the ground mustard seed, the edible salt and the edible oil are contained within a capsule.

* * * * *